United States Patent [19]
Tanaka

[11] Patent Number: 5,640,963
[45] Date of Patent: Jun. 24, 1997

[54] EYE FUNDUS BLOOD FLOW METER

[75] Inventor: Shinya Tanaka, Tokyo, Japan

[73] Assignee: Canon Kabushiki Kaisha, Tokyo, Japan

[21] Appl. No.: 350,163

[22] Filed: Nov. 30, 1994

[30] Foreign Application Priority Data

Dec. 3, 1993 [JP] Japan ............................ 5-339469
Mar. 17, 1994 [JP] Japan ............................ 6-071329

[51] Int. Cl.⁶ .................................................. A61B 5/00
[52] U.S. Cl. ............................ 128/665; 128/691; 128/633
[58] Field of Search ........................ 128/653.1, 633, 128/637, 664, 665, 691; 356/28, 28.5, 39; 351/221

[56] References Cited

U.S. PATENT DOCUMENTS

| | | | |
|---|---|---|---|
| 4,142,796 | 3/1979 | Riva | 356/28.5 |
| 4,166,695 | 9/1979 | Hill et al. | 356/28.5 |
| 4,346,991 | 8/1982 | Gardner et al. | 351/221 |
| 4,402,601 | 9/1983 | Riva | 351/221 |
| 4,579,430 | 4/1986 | Bille | 128/633 |
| 4,856,891 | 8/1989 | Pflibsen et al. | 351/210 |
| 4,950,070 | 8/1990 | Aizu et al. | 128/691 |
| 5,058,596 | 10/1991 | Makino et al. | 128/691 |
| 5,090,416 | 2/1992 | Ogino et al. | 128/691 |
| 5,094,523 | 3/1992 | Reznichenko et al. | 351/221 |
| 5,106,184 | 4/1992 | Milbocker | 351/221 |
| 5,394,199 | 2/1995 | Flower | 128/691 |
| 5,437,274 | 8/1995 | Khoobehi et al. | 128/691 |

*Primary Examiner*—Marvin M. Lateef
*Assistant Examiner*—Brian L. Casler
*Attorney, Agent, or Firm*—Fitzpatrick, Cella, Harper & Scinto

[57] ABSTRACT

An eye fundus blood flow meter has probing beam applying device for applying probing beam to a blood vessel on the fundus of an eye to be examined, a light receptor for receiving the scattered light of the probing beam from the vicinity of the blood vessel from two different directions of light reception, a signal processor for obtaining the information of the blood flow speed in the blood vessel on the basis of Doppler shift information in the output from the light receptor, and changing device for changing the angle of incidence of the probing beam onto the fundus of the eye or the two directions of light reception of the light receptor.

17 Claims, 6 Drawing Sheets

EYE FUNDUS BLOOD FLOW METER

BACKGROUND OF THE INVENTION

1. Field of the Invention

This invention relates to an eye fundus blood flow meter for measuring a blood flow in a blood vessel on the fundus of an eye to be examined.

2. Related Background Art

Figure 1A:
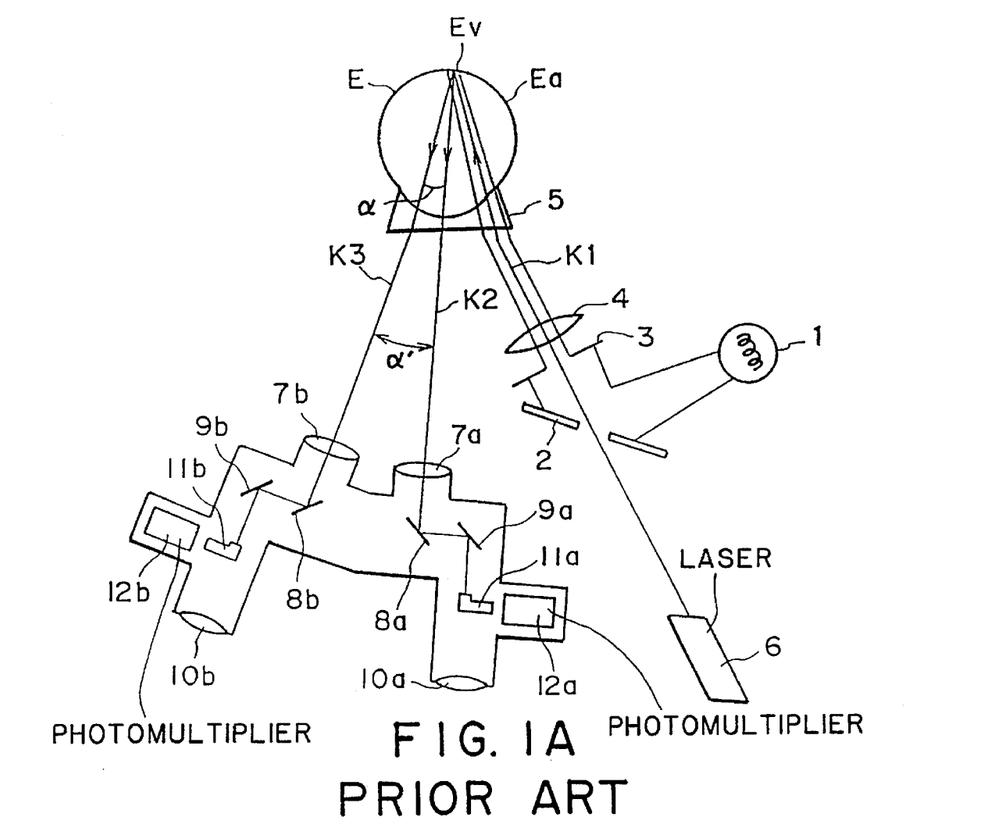
FIG. 1A shows the construction of an example of the prior art.

FIG. 1A of the accompanying drawings shows an example of an eye fundus blood flow meter according to the prior art which is an improvement over a slit lamp generally used for ophthalmic diagnosis and treatment. An illuminating optical system is disposed on an optical path K1, and a white beam of light from an illuminating light source 1 is reflected by an apertured mirror 2 and illuminates a blood vessel Ev on the fundus Ea of an eye E to be examined through a slit 3, a lens 4 and a contact lens 5 which offsets the refractive power of the cornea of the eye E to be examined to thereby enable the fundus Ea of the eye to be observed. A laser light source 6 for measurement emitting He-Ne laser light is disposed on an optical path behind the apertured mirror 2, and the probing beam from the laser light source 6 for measurement passes through the central opening portion of the apertured mirror 2, is made coaxial with the beam of light from the illuminating light source 1 and irradiates the fundus Ea of the eye in the form of a point.

A beam of light scattered and reflected by Red blood cells flowing through the blood vessel Ev and the wall of the blood vessel passes through the objective lenses 7a, 7b of a light detecting optical system for stereoscopic observation disposed on optical paths K2 and K3 forming an angle α'therebetween, is reflected by mirrors 8a, 8b and mirrors 9a, 9b and is observed as the image of the fundus of the eye by an examiner through eyepieces 10a, 10b, and the examiner selects a measured region while looking into the eyepieces 10a, 10b and observing the fundus Ea of the eye.

Figure 1B:
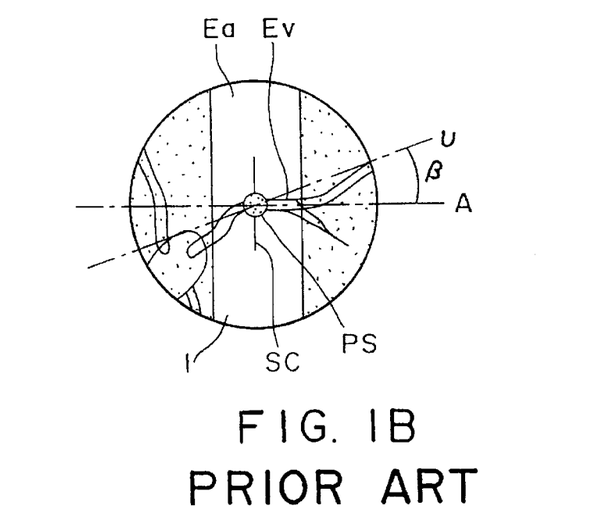
FIG. 1B is an illustration of the image of the fundus of an eye observed.

FIG. 1B of the accompanying drawings shows the image of the fundus of the eye observed by the examiner. When in an area I being illuminated by the illuminating light, the blood vessel Ev which is the object of measurement is aligned with a scale SC prepared in advance on the focal plane of the eyepieces 10a, 10b, the probing beam from the laser light source 6 for measurement and the blood vessel Ev are aligned with each other, and the measured region is indicated by a spot beam of light PS formed by the laser light source 6 for measurement. At this time, the reflected beam of light of the probing beam by the fundus Ea of the eye is detected by photomultipliers 12a, 12b through optical fibers 11a, 11b.

This detection signal by photomultipliers includes a beat signal component created by a component Doppler-shifted by a blood flow flowing through the blood vessel Ev and a component reflected by the stationary blood vessel wall interfering with each other, and this beat signal is frequency-analyzed to thereby find the speed of the blood flow in the blood vessel Ev.

Figure 1C:
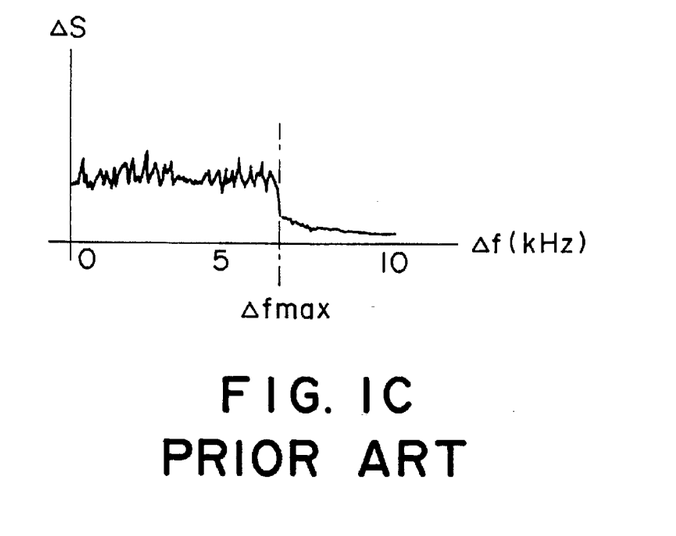
FIG. 1C is a graph of the frequency distribution of a light reception signal.

FIG. 1C of the accompanying drawings shows an example of the result of the frequency analysis of the detection signal by the photomultipliers 12a, 12b, and in this figure, the axis of abscissas represents a frequency $\Delta f$ and the axis of ordinates represents the power $\Delta S$ thereof. The relation among the maximum shift $\Delta f_{max}$ of the frequency, the wave number vector $\kappa i$ of the incident beam of light, the wave number vector $\kappa s$ of the received beam of light and the speed vector $v$ of the blood flow can be expressed as $$\Delta f_{max} = (\kappa s - \kappa i) \cdot v. \qquad (1)$$

Accordingly, modifying expression (1) by the use of the shifts $\Delta f_{max}1$ and $\Delta f_{max}2$ of the frequency calculated from the respective light detection signals by the photomultipliers 12a and 12b, the wavelength $\lambda$ of the laser light, the refractive index n of the measured region, the angle α formed between light detecting optical axes K2 and K3 in the eye and the angle β formed between a plane made by the light detecting optical axes K2 and K3 in the eye and the speed vector v of the blood flow, the maximum speed Vmax of the blood flow can be expressed as $$V_{max} = \{\lambda/(n\alpha)\} \cdot |\Delta f_{max}1 - \Delta f_{max}2|/\cos\beta. \qquad (2)$$

Thus, by effecting measurement from two directions, the contribution in the direction of incidence of the probing beam is offset, whereby a blood flow in any region on the fundus Ea of the eye can be measured.

Also, to measure the true speed of the blood flow from the relation between the line of intersection A of the plane made by the two light detecting optical paths K2, K3 with the fundus Ea of the eye and the angle β formed between this line of intersection A and the speed vector v of the blood flow, it is necessary to make the line of intersection A coincident with the speed vector v with β=0° in expression (2). Therefore, in the example of the prior art, the entire light detecting optical system is rotated or an image rotator is disposed in the light receiving optical system, thereby making the line of intersection A optically coincident with the speed vector v.

In the above-described example of the prior art, however, the maximum value $\Delta f_{max}$ of the Doppler shift is detected as the interference signal between the component shifted by the blood flow and the stationary blood vessel wall and thus, the maximum shift $\Delta f_{max}$ obtained by frequency analysis becomes $|\Delta f_{max}|$ which lacks sign information.

Thus, when measuring the blood flows in blood vessels in different regions of the fundus Ea of the eye, there are cases where the signs of the maximum frequency shifts $\Delta f_{max}1$ and $\Delta f_{max}2$ both have the positive sign, both have the negative sign, and have the positive and the negative sign, respectively. Accordingly, this gives a rise to a problem that depending on the area to be measured, it becomes impossible to determine the maximum blood flow speed Vmax by expression (2).

This problem will now be described by the use of FIG. 1D of the accompanying drawings. When in FIG. 1D, signal light enters from the center hi=0 of the pupil Ep and scattered light is received from the predetermined regions hs1 and hs2 of the pupil Ep, the angle at which the predetermined regions hs1 and hs2 are subtended from the fundus Ea of the eye is the angle α formed between the light detecting optical axes in the example of the prior art shown in FIG. 1A.

Considering now a case where a blood vessel Ev1 at the center of the fundus Ea of the eye and a blood vessel Ev2 in the marginal region of the fundus Ea of the eye are to be measured, when the measurement of the blood vessel Ev1 is effected, the maximum frequency shift $\Delta f_{max}1$ obtained by the light reception signal from the direction of the region hs1 and the maximum frequency shift $\Delta f_{max}2$ obtained by the light detection signal from the direction of the region hs2 assume different signs. In this case, the signal light is incident on the blood vessel Ev1 perpendicularly thereto and thus, the frequency shift caused by the direction of the signal light is null and the frequency shift obtained is only caused by the direction of observation. Considering here the speed vector υ of the blood flow in the blood vessel Ev1, the wave number vector κs1 in the direction of hs1 and the wave number vector κs2 in the direction of hs2, these exist in different directions relative to the perpendicular to the speed vector υ and therefore, the inner product thereof assumes a different sign and frequency shifts of different signs occur.

On the other hand, when the measurement of the blood vessel Ev2 in the marginal region is effected, the direction of hs1 and the direction of hs2 exist in the same direction relative to positive reflected light κ' whose frequency shift is 0 and thus, frequency shifts of the same sign occur. Here, the angle formed between a straight line linking the center Eo of the fundus Ea of the eye and the blood vessel Ev2, i.e., the perpendicular at the blood vessel Ev2 of the fundus Ea of the eye, and the direction of the wave number vector κi of the signal light is φi, and a wave number vector indicative of the positive reflected light of the vector κi being at an angle φc with respect to the perpendicular and facing in opposite direction to the vector κi is κi'.

SUMMARY OF THE INVENTION

It is an object of the present invention to solve the above-noted problems and to provide an eye fundus blood flow meter which can effect the detection of the above-described sign determining area and can always effect correct measurement irrespective of the region and direction of the blood vessel on the fundus of an eye.

Other objects of the present invention will become apparent from the following detailed description of some embodiments of the invention.

DETAILED DESCRIPTION OF THE PREFERRED EMBODIMENTS

A first embodiment of the present invention will hereinafter be described in detail with reference to FIGS. 2 to 4.

Figure 2:
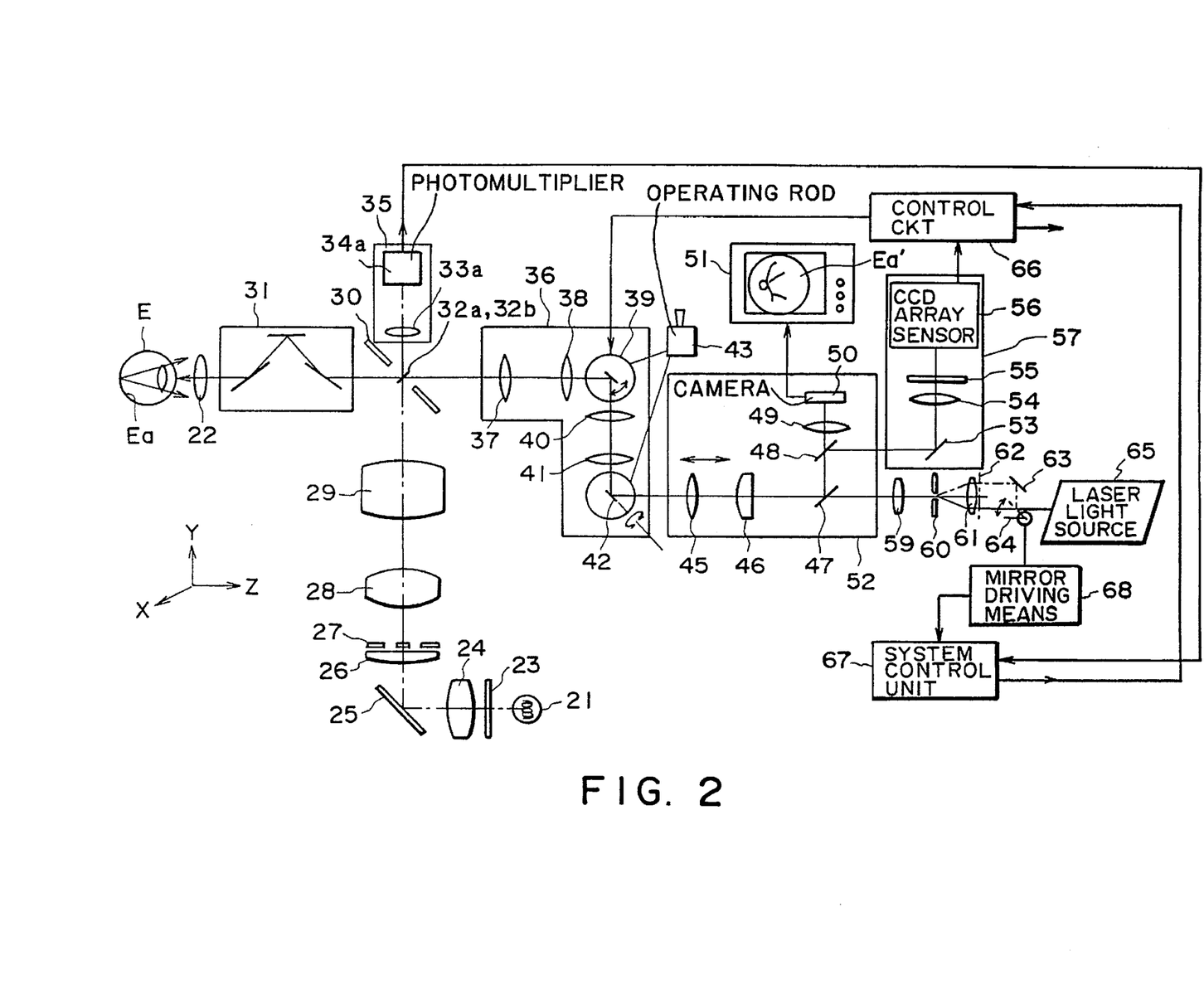
FIG. 2 shows the construction of an embodiment of the present invention.

Referring to FIG. 2 which shows the construction of an eye fundus blood flow meter according to the present embodiment, a band-pass filter 23 transmitting only yellow and green beams of light therethrough, a condenser lens 24, a mirror 25, a field lens 26, a ring slit 27, relay lenses 28, 29, an apertured mirror 30 and an image rotator 31 are disposed on an optical path leading from an illuminating light source 21 comprising a tungsten lamp or the like emitting white light to an objective lens 22. Light detecting optical system 35 in which a pair of small mirrors 32a, 32b, a pair of lenses 33a, 33b and a pair of photomultipliers 34a, 34b are disposed on optical paths extending upwardly in two directions from the opening portion of the apertured mirror 30. In FIG. 2, in order to avoid duplication, only the members on the optical axis of the small mirror 32a of the pair of small mirrors 32a, 32b are shown.

An image stabilizer 36 is disposed on an optical path behind the apertured mirror 30, and lenses 37, 38, a galvanometric mirror 39, lenses 40, 41 and a galvanometric mirror 42 are disposed in succession in the image stabilizer 36. The galvanometric mirrors 39 and 42 are rotatable by means of an operating rod 43, the galvanometric mirror 39 is rotated about a rotational axis perpendicular to the plane of the drawing sheet of FIG. 2 and the galvanometric mirror 42 is rotated about a rotational axis parallel to the plane of the drawing sheet orthogonal to the first-mentioned rotational axis.

A focusing lens 45, a lens 46 and a dichroic mirror 47 which are movable along the optical axis are disposed on an optical path behind the galvanometric mirror 42, and a half mirror 48, a lens 49 and a television camera 50 are disposed on an optical path in the direction of reflection of the dichroic mirror 47, whereby an observation optical system 52 is constituted, and the output of the television camera 50 is connected to a television monitor 51. Also, a mirror 53, a lens 54, a filter 55 and a one-dimensional CCD array sensor 56 with an image intensifier are disposed on an optical path in the direction of reflection of the half mirror 48, whereby a blood vessel detecting system 57 is constituted. The dichroic mirror 47 is made conjugate with the galvanometric mirrors 39 and 42.

At the passage side of the dichroic mirror 47, there are disposed a lens 59, an aperture 60 lying at a location conjugate with the fundus Ea of an eye E to be examined, an imaging lens 61 and a laser optical system for measurement emitting laser light which is signal light. The laser optical system for measurement is constituted by an aperture 62 with two holes, a fixed mirror 63 disposed rearwardly of one of the holes in the aperture 62, an optical path switching mirror 64 disposed rearwardly of the other hole in the aperture 62, and a laser light source 65 for measurement disposed rearwardly of the switching mirror 64, and the aperture 62 with two holes is at a location substantially conjugate with the dichroic mirror 47, the pupil of the eye E to be examined and the two galvanometric mirrors 39, 42.

The output of the CCD array sensor 56 is connected to a control circuit 66 which has a blood vessel image analyzing circuit constituted by a tuning memory circuit, a memory processing circuit, a control unit, etc. and whose output is connected to the galvanometric mirror 39. The output of a system control unit 67 is connected to the control circuit 66, and the output of the system control unit 67 is also connected to mirror driving means 68 for driving the optical path switching mirror 64. The outputs of the photomultipliers 34a and 34b are connected to the system control unit 67.

Figure 3:
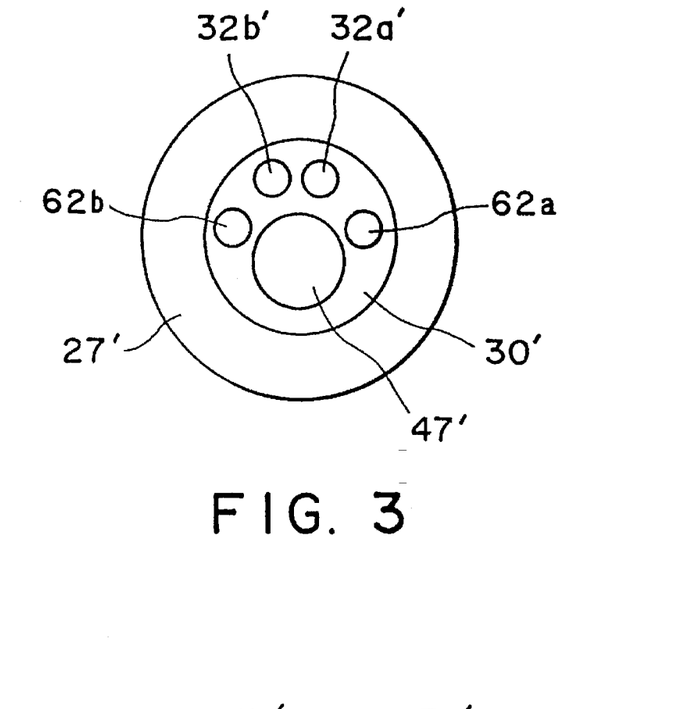
FIG. 3 is an illustration of the arrangement of beams of light on the pupil.

FIG. 3 shows the arrangement of beams of light relative to the pupil of the eye E to be examined. The image 27' of the ring slit 27 indicates the position of the illuminating beam of light for the whole of the fundus Ea of the eye, the images 32a' and 32b' of the pair of small mirrors 32a and 32b indicate the positions of the received beams of light of a Doppler signal, and the images 62a' and 62b' of the two hole portions 62a and 62b of the aperture 62 with two holes in the laser optical system for measurement indicate the positions of the incident beams of light of laser light which is signal light. Also, the image 30' of the opening portion of the apertured mirror 30 and the image 47' of the dichroic mirror 47 indicate the positions of beams of light for observation.

The illuminating beam of light from the illuminating light source 21 is imaged on the opening portion of the ring slit 27 via the band-pass filter 23, the condenser lens 24, the mirror 25 and the field lens 26, and is again imaged on the apertured mirror 30 by the relay lenses 28, 29, whereafter it passes through the image rotator 31 and the objective lens 22, is imaged as the slit ring image 27' on the pupil of the eye E to be examined, and substantially uniformly illuminates the fundus Ea of the eye.

The reflected light by the fundus Ea of the eye is taken out from the image 30' of the opening portion of the apertured mirror 30, returns along the same optical path, passes from the opening portion of the apertured mirror 30 and through the lenses 37, 38, galvanometric mirror 39, lenses 40, 41 and the galvanometric mirror 42 of the image stabilizer 36, is reflected by the dichroic mirror 47 via the focusing lens 45 and the lens 46, passes through the half mirror 48 and the lens 49, is imaged as an eye fundus image Ea' on the television camera 50 and is displayed on the television monitor 51. An examiner effects the alignment of the apparatus and the selection of a measured region while observing the television monitor 51.

Also, the beam of light reflected by the half mirror 48 passes through the mirror 53, lens 54 and filter 55 of the blood vessel detecting system 57 and is received by the CCD array sensor 56 as a blood vessel image Ev' more enlarged than the eye fundus image Ea' picked up by the television camera 50. The output signal from the CCD array sensor 56 is processed into data indicative of the amount of movement of the blood vessel Ev, in the blood vessel image analyzing circuit in the control circuit 66, whereafter the galvanometric mirror 39 is driven and controlled so that said amount of movement may be compensated for by the control circuit 66.

On the other hand, the signal light from the laser light source 65 for measurement passes through one hole 62a in the aperture 62 with two holes because the optical path switching mirror 64 deviates from the optical path, whereafter it passes through the aperture 60 for specifying the measured region by the image lens 61, and thereafter reversely returns along the above-mentioned optical path and is projected onto the blood vessel Ev on the fundus Ea of the eye E to be examined with the position of the beam of light specified by the image 62a' of the opening portion of the aperture 62 with two holes on the pupil through the objective lens 22.

The hole portions 62a and 62b of the aperture 62 with two holes are imaged outside the image 47' of the dichroic mirror 47 lying at the conjugate location and therefore, the signal light is not eclipsed by the dichroic mirror 47 and the reflected beam of light from the blood vessel Ev returns along the same optical path and a part thereof is reflected in two directions by the pair of small mirrors 32a and 32b. The beams of light reflected by the pair of small mirrors 32a and 32b, respectively, are beams of light taken out from mirror images 32a' and 32b' on the pupil, and are imaged on the photomultipliers 34a and 34b, respectively, via the lenses 33a and 33b. These light reception signals are sent to the system control unit 67 for the measurement of flow speed, and frequency analysis is effected therein as in the example of the prior art.

On the other hand, the beam of light which is not reflected by the pair of small mirrors 32a and 32b is a beam of light taken out from the opening image 30' on the pupil, and passes through the opening portion of the apertured mirror 30, the image stabilizer 36, the focusing lens 45 and the lens 46, and a part of it is reflected by the dichroic mirror 47 and is formed as a spot image on the television camera 50 via the half mirror 48 and the lens 49, and is displayed on the television monitor 51 with the eye fundus image Ea' by the illuminating light source 21 and acts on the index mark of the measured region.

The reflected beam of light on the fundus Ea of the eye by the laser light source 65 for measurement enters the blood vessel detecting system 57 via the half mirror 48, but since the filter 55 intercepts the wavelength of the laser light source 65 for measurement, the CCD array sensor 56 picks up only the blood vessel image Ev' by the illuminating light source 21.

The probing beam from the laser light source 65 for measurement is imaged on the focal plane of the aperture 60 in which the imaging lens 61 is conjugate with the fundus Ea of the eye E to be examined, and that conjugate relation is adjusted by the focusing lens 45. Accordingly, when the examiner operates a focusing knob, not shown, to thereby effect focusing, the focusing lens 45 is moved along the optical axis and the image pickup surface of the television camera 50, the image pickup surface of the CCD array sensor 56 and the focal plane of the aperture 60 of the lens 61 become conjugate with the fundus Ea of the eye at a time, and a spot image PS is also focused with the eye fundus image Ea'.

Figure 4:
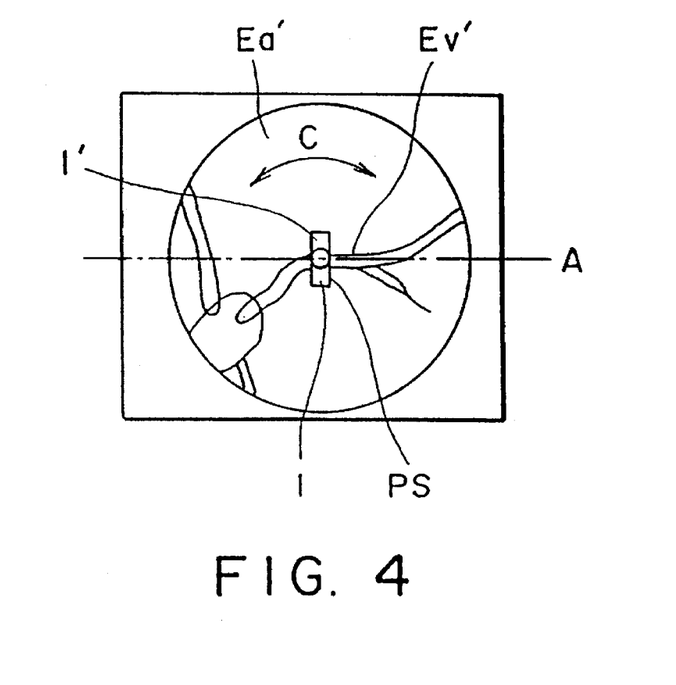
FIG. 4 is an illustration of the image of the fundus of an eye observed.

At this time, the eye fundus image Ea' is displayed on the television monitor 51, as shown in FIG. 4. The above-mentioned spot image PS is fixed at the center of the field of view and therefore, the selection of the measured region is effected by bringing the spot image PS into coincidence with a predetermined measured region by means of the operating rod 43, rotating the image rotator 31 and aligning the blood vessel image Ev' which is the object of measurement with an axis A. The direction of the coordinates axis A indicates the direction of the line of intersection of a plane linking the centers of the pair of small mirrors 32a and 32b with the fundus Ea of the eye, and is displayed on the television monitor 51 as an index mark for adjusting the image rotator 31. When the examiner rotates the image rotator 31, the image Ea' of the fundus of the eye E to be examined rotates as indicated by arrow C.

By bringing the blood vessel Ev into coincidence with the axis A to thereby provide $\beta=0°$ in FIG. 1B, there are obtained the following advantages (a), (b) and (c):

(a) When from expression (2), $\beta=90°$, that is, cos $\beta=0$, it becomes impossible to obtain the absolute value of the maximum blood flow speed Vmax from the maximum frequency shifts $\Delta$fmax1 and $\Delta$fmax2, but if the eye fundus image Ea' is rotated so that $\beta=0°$, the unmeasurable position can be avoided.

(b) Since it becomes unnecessary to measure the angle $\beta$, error factors decrease and the work is simplified.

(c) As described with respect to the example of the prior art, the blood flow speed is found from the interference signal between the scattered reflected light from the blood vessel wall and the scattered reflected light in the blood and therefore, even when during measurement, the fundus Ea of the eye moves in the direction of the axis A, the result of measurement will not be affected if the blood vessel Ev is made substantially parallel to the direction of the axis A.

On the other hand, when the fundus Ea of the eye moves in the axial direction orthogonal to the axis A, the signal light from the laser light source 65 for measurement deviates from the blood vessel Ev in the measured region and the measured value becomes unstable, but in such case, the amount of movement of the blood vessel Ev can be detected only with respect to that direction and therefore, in the present embodiment, tracking only in that one direction is effected by the blood vessel detecting system 57 and the image stabilizer 36.

In this tracking, to measure the blood flow speed accurately and quickly with respect to any blood vessel Ev to be detected, the CCD array sensor 56 for detecting the amount of movement of the blood vessel image Ev' can be disposed perpendicularly to the blood vessel image Ev' which is the object of measurement, and further by providing $\beta=0°$, it becomes unnecessary to use any two-dimensional sensor.

In the present embodiment, the elements of the CCD array sensor 56 are arranged in a direction orthogonal to the axis A, and when the selection of the measured region has been completed as shown in FIG. 3, the CCD array sensor 56 of the blood vessel detecting system 57 enlarges the eye fundus image Ea' indicated by a bar-like area I in the direction orthogonal to the axis A and picks it up as the blood vessel image Ev'.

When the examiner depresses a measuring switch, not shown, to start measurement after the alignment has been thus completed, the system control unit 67 receives this signal and imparts a tracking start command to the control circuit 66. At the same time, the signals of the photomultipliers 34a and 34b are introduced into the system control unit 67 and the maximum frequency shifts |Δfmax1| and |Δfmax2| by the signal light entering from the location of the hole portion image 62a' of the aperture 62 on the pupil of the eye E to be examined are first found. The maximum frequency shift |fmax1| is the result of the processing of the output signal from the photomultiplier 34a, and the maximum frequency shift |Δfmax2| is the result of the processing of the output signal from the photomultiplier 34b.

Here, the incident signal light is located on the hole portion image 62a' and is provided at a location in the same direction relative to the positions 32a' and 32b' of the received beams of light and therefore, if usual, the maximum speed Vmax will be found by providing cos $\beta=1$ in expression (2) and by Vmax={$\lambda/(n\alpha)$}·||Δfmax1|−|Δfmax2||, but depending on the location of the blood vessel Ev on the fundus of the eye, there is also a case where the true flow speed must be Vmax={$\lambda/(n/\alpha)$}·||Δfmax1|+|Δfmax2||. In the present embodiment, at first, as pre-measurement, the maximum speed Vmax by expression (2) is calculated in this state, whereafter the optical path switching mirror 64 is inserted into the optical path by the output of the system control unit 67 and the signal light is caused to enter from the other hole portion 62b of the aperture 62 with two holes to thereby effect measurement.

The hole portion image 62b' which this hole portion 62b makes on the pupil of the eye E to be examined is disposed so as to have its center on a straight line passing through the center of the other hole portion image 62a' and parallel to a straight line linking the centers of the images 32a' and 32b' of the pair of small mirrors 32a and 32b, as shown in FIG. 3, and particularly in the present embodiment, the spacing thereof is selected so as to be greater than the distance between the centers of the images 32a' and 32b' and so that a straight line linking the midpoints of two straight lines (a straight line linking the centers of the images 32a' and 32b' and a straight line parallel thereto and passing through the center of the hole portion image 62a') is orthogonal to the straight line linking the respective centers.

Figure 1D:
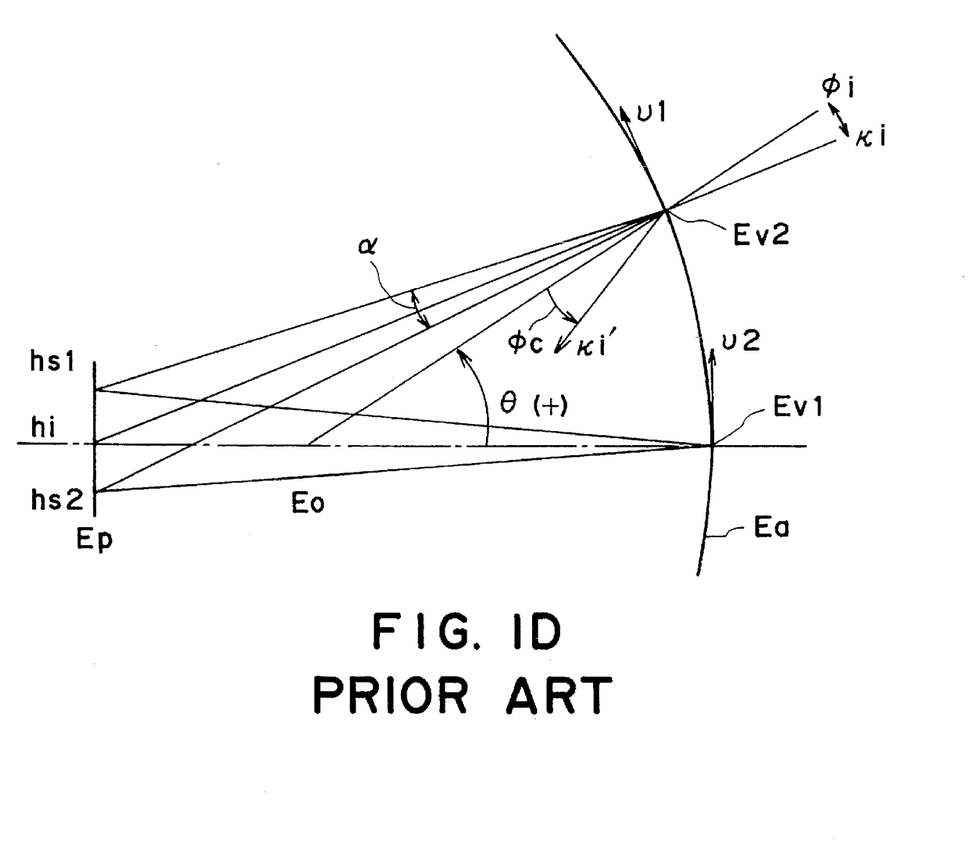
FIG. 1D is an illustration of the arrangement of beams of light in the eye.

After the position of the incident beam of light has been switched from the hole portion image 62a' of the aperture 62 to the thus selected hole portion image 62b', the system control unit 67 again introduces signals from the two photomultipliers 34a and 34b, calculates respective maximum frequency shifts |Δfmax1'| and |Δfmax2'| and calculates the maximum speed Vmax in accordance with expression (2), and when the maximum speed Vmax at this time is placed as Vmax', it becomes possible to select the incident beam of light as described above to thereby separate the area of the angle $\phi i$ in FIG. 1D in which the signs of the maximum frequency shifts |Δfmax1| and |Δfmax2| are switched and an area in which the signs of the maximum frequency shifts |Δfmax1'| and |Δfmax2'| are switched. In an area wherein the signs are not switched, Vmax≡Vmax'. Also, in an area wherein the sign of one of the maximum speeds Vmax and Vmax' is switched, it becomes possible to create the relation that (the side on which the switching of the sign does not take place)>(the side on which the switching of the sign takes place).

Accordingly, in the apparatus of the present embodiment, the system control unit 67 can determine the direction of incidence of appropriate signal light for finding a true maximum flow speed, by comparing the two maximum speeds Vmax and Vmax' with each other. By this information, the system control unit 67 brings the optical path switching mirror 64 into an appropriate state (for example, when Vmax≠Vmax', it brings the optical path switching mirror 64 into a state in which the greater speed has been detected) and controls it so as to effect main measurement, and in the main measurement, it repeats the measurement and calculation of the maximum speed Vmax or Vmax' at suitable time intervals, whereby continuous measurement is effected.

In the present embodiment, there has been shown a method of judging the maximum speeds Vmax and Vmax' before the main measurement, but instead of this, it is also possible to cope with the situation using software for measuring and calculating the maximum speeds Vmax and Vmax' before the main measurement, and then checking the presence or absence of the reversal of the sign and for example, reversing the sign of the calculation of expression (2) by the presence or absence of the reversal of the sign.

As described above, according to the eye fundus blood flow meter of the above-described embodiment, when detecting the Doppler shifts created from two directions by the blood flow on the fundus of the eye, it becomes possible to switch the direction of incidence of the probing beam therefor and effect the measurement of the blood flow speeds, and compare the results of the measurement with each other to thereby avoid the problem of the reversal of the sign of the measurement signal. Thus, it is possible to measure always a correct blood flow speed for any blood vessel existing at any location and in any direction in the eyeball.

A second embodiment of the present invention will now be described in detail with reference to FIGS. 5 to 8 although the description may include some duplication with the description of the first embodiment.

Figure 5:
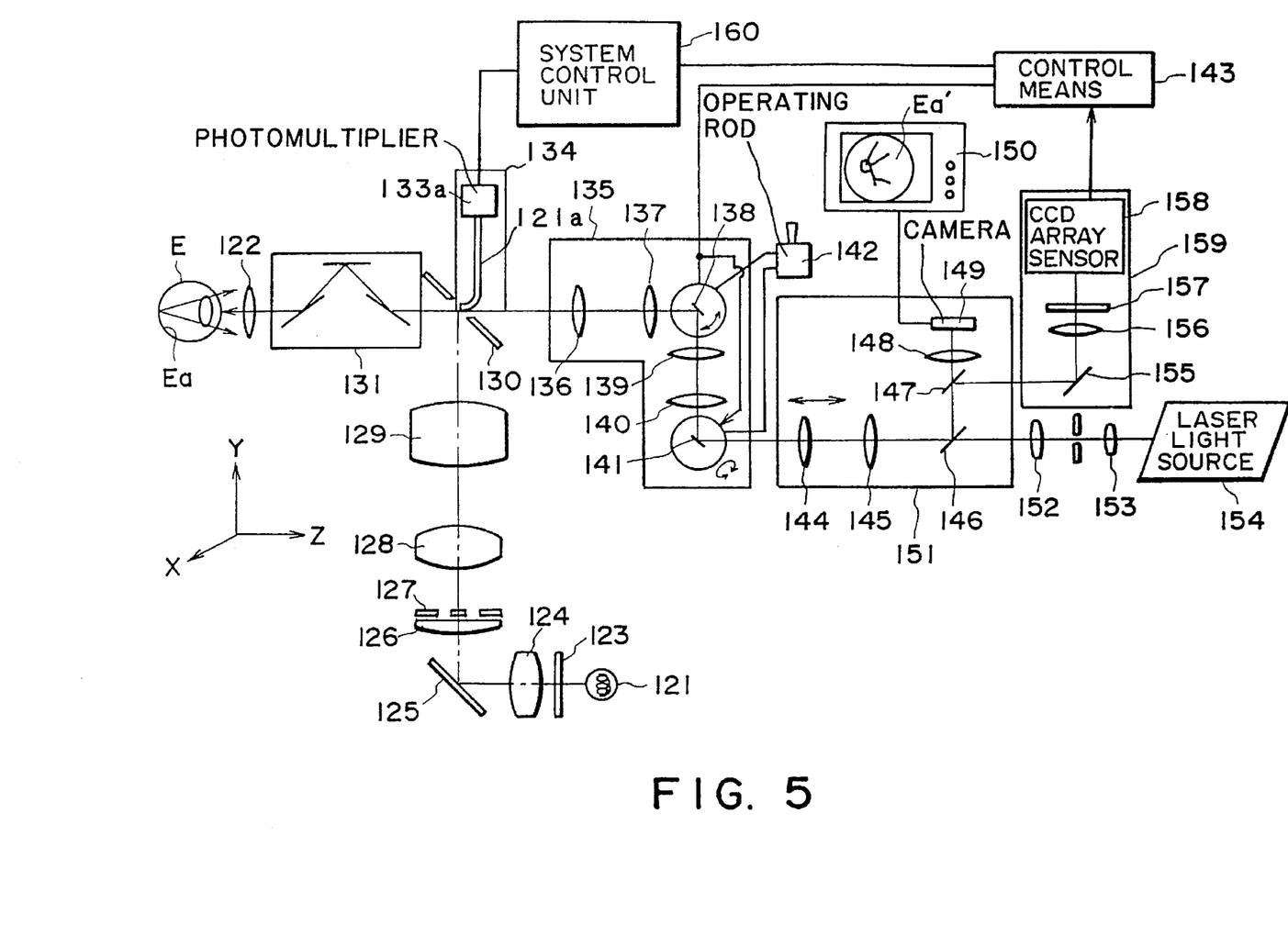
FIG. 5 shows the construction of another embodiment of the present invention.

Referring to FIG. 5 which shows the construction of a second embodiment of the eye fundus blood flow meter of the present invention, a band-pass filter 123 transmitting only yellow and green beams of light therethrough, a condenser lens 124, a mirror 125, a field lens 126, a ring slit 127, relay lenses 128, 129, an apertured mirror 130 and an image rotator 131 are disposed in succession on an optical path leading from an illuminating light source 121 such as a tungsten lamp emitting white light to an objective lens 122.

Figure 6:
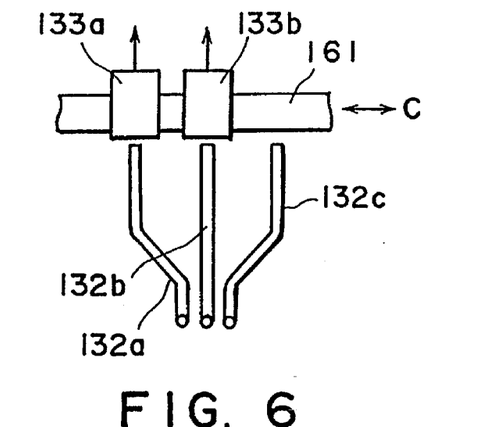
FIG. 6 is an illustration of the arrangement of optical fibers and photomultipliers.

In the opening portion of the apertured mirror 130, there are provided optical fibers 132a, 132b and 132c for directing scattered light from the fundus Ea of the eye as shown in FIG. 6, and photomultipliers 133a and 133b selectively connected to the optical fibers 132a, 132b and 132c are further disposed, whereby a light receiving optical system 134 is constituted. In FIG. 5, only the optical fiber 121a and photomultiplier 133a are shown to avoid duplication.

An image stabilizer 135 is disposed on an optical path behind the apertured mirror 130, lenses 136, 137, a galvanometric mirror 138, lenses 139, 140 and a galvanometric mirror 141 are provided in succession in the image stabilizer 135, the galvanometric mirrors 138 and 141 are rotatable by means of an operating rod 142, the galvanometric mirror 138 has a rotational axis in a direction orthogonal to the plane of the drawing sheet of FIG. 5, and the galvanometric mirror 141 has a rotational axis in a direction parallel to the plane of the drawing sheet of FIG. 5. Further, the output of control means 143 is connected to the galvanometric mirror 138.

A focusing lens 144, a lens 145 and a dichroic mirror 146 which are movable along the optical axis are disposed on an optical path behind the galvanometric mirror 141, a half mirror 147, a lens 148 and a television camera 149 are disposed on an optical path in the direction of reflection of the dichroic mirror 146, and the output of the television camera 149 is connected to a television monitor 150, whereby an observation optical system 151 is constituted. The dichroic mirror 146 is made conjugate with the galvanometric mirrors 138 and 141.

At the passage side of the dichroic mirror 146, there are disposed a lens 152, an imaging lens 153 whose focal plane is at a location conjugate with the fundus Ea of the eye, and a probing beam source 154 emitting laser light which is signal light. Also, a mirror 155, a lens 156, a filter 157 and a CCD array sensor 158 with an image intensifier are disposed on an optical path in the direction of reflection of the half mirror 147, whereby a blood vessel detecting system 159 is constituted. The output of the CCD array sensor 158 is connected to the control means 143, in which is contained a blood vessel image analyzing circuit constituted by a tuning memory circuit, a memory processing circuit, a control unit, etc. Further, the photomultipliers 133a, 133b and the control means 143 are connected to a system control unit 160.

The entrance ends of the three optical fibers 132a, 132b and 132c are arranged on a straight line in the opening portion of the apertured mirror 130 as shown in FIG. 6, and the exit ends thereof are fixed likewise on a straight line with the gaps therebetween widened. Rearwardly of the exit ends, the photomultipliers 133a and 133b are individually supported by a support member 161 for movement in the direction of arrow C. There is shown a state in which the emergent light from the optical fiber 132a is received by the photomultiplier 133a and the emergent light from the optical fiber 132b is received by the photomultiplier 133b, but when the support member 161 is moved by an actuator, not shown, with the aid of the system control unit 160, the state changes over to a state in which the emergent light from the optical fiber 132b is received by the photomultiplier 133a and the emergent light from the optical fiber 132c is received by the photomultiplier 133b.

The illuminating beam of light from the illuminating light source 121 is imaged on the opening portion of the ring slit 127 via the band-pass filter 123, the condenser lens 124, the mirror 125 and the field lens 126, and is once imaged on the apertured mirror 130 by the relay lenses 128 and 129, whereafter it passes through the image rotator 131 and the objective lens 122, is imaged on the pupil of the eye E to be examined and illuminates the fundus Ea of the eye substantially uniformly.

Figure 7:
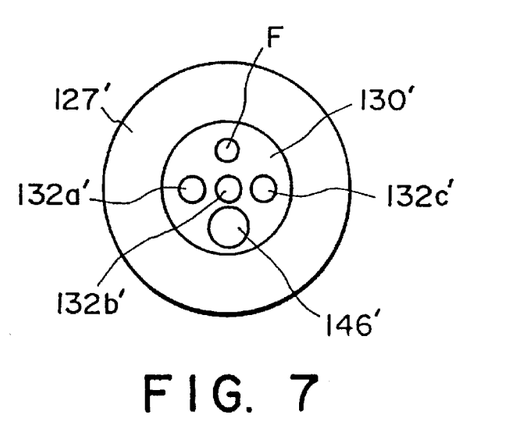
FIG. 7 is an illustration of the arrangement of beams of light in the pupil.

FIG. 7 shows the positions of the beams of light relative to the pupil of the eye E to be examined, the image 127' of the ring slit indicates the position of the illuminating beam of light on the entire fundus Ea of the eye, the images 132a', 132b' and 132c' of the end surfaces of the light receiving optical fibers indicate the positions of the received beams of light, the image F of the focal plane of the imaging lens 153 of the measuring laser optical system indicates the position of the incident beam of light of the laser light, and the image 130' of the apertured mirror 130 and the image 146' of the dichroic mirror 146 indicate the position of the beam of light for observation.

The reflected light on the fundus Ea of the eye is taken out from the image 130' of the apertured portion of the apertured mirror 130 in the pupil and returns along the same optical path, passes through the apertured portion of the apertured mirror 130, passes through the lenses 136, 137, galvanometric mirror 138, lenses 139, 140 and galvanometric mirror 141 of the image stabilizer 135, is further reflected by the dichroic mirror 146 via the focusing lens 144 and the lens 145, passes through the half mirror 147 and the lens 148, is imaged as an eye fundus image Ea' on the television camera 149 and is displayed on the television monitor 150. The examiner effects the alignment of the apparatus and the selection of a measured region while observing the television monitor 150.

The beam of light reflected by the half mirror 147 passes through the mirror 155, lens 156 and filter 157 of the blood vessel detecting system 159, and is received by the CCD array sensor 158 as a blood vessel image more enlarged than the eye fundus image Ea' picked up by the television camera 149. The output signal from the CCD array sensor 158 is processed into data representative of the amount of movement of the blood vessel Ev in the blood vessel image analyzing circuit, whereafter the control means 143 drives and controls the galvanometric mirror 138 so as to compensate for that amount of movement.

On the other hand, the signal light from the measuring laser light source 154 is condensed by the imaging lens 153 and returns along the previously described optical path, and is projected from the position F of the beam of light shown in FIG. 7 onto the blood vessel on the fundus Ea of the eye E to be examined through the objective lens 122. This position F of the beam of light is disposed outside the dichroic mirror 146 lying at a conjugate location and therefore, the signal light is never eclipsed by the dichroic mirror 146.

The reflected beam of light from the blood vessel returns along the same optical path and a part of it is directed to the light receiving optical system by the optical fibers 132a, 132b and 132c. When the light receiving optical system is in the state shown in FIG. 6, the beams of light received by the photomultipliers 133a and 133b are beams of light located at 132a' and 132b' in FIG. 7 on the pupil, and as in the example of the prior art, frequency analysis for the measurement of the blood flow speed is effected by the use of this light reception signal.

On the other hand, the beam of light not received by the optical fibers 132a, 132b and 132c is a beam of light taken out from the opening image 130' on the pupil, and passes through the opening portion of the apertured mirror 130, the image stabilizer 135, the focusing lens 144 and the lens 145, and a part of it is reflected by the dichroic mirror 146, is formed as a spot image by the television camera 149 via the half mirror 147 and the lens 148, is displayed on the television monitor 150 with the eye fundus image Ea' by the illuminating light source 121 and acts as an index mark for the measured region.

The reflected beam of light on the fundus Ea of the eye by the measuring laser light source 154 enters the blood vessel detecting system 159 via the half mirror 147, but since the filter 157 intercepts the wavelength of the measuring laser light source 154, only the blood vessel image by the illuminating light source 121 is picked up by the CCD array sensor 158.

The measuring laser beam is condensed by the focal plane of the imaging lens 153 and the conjugate relation thereof is adjusted by the focusing lens 144. Accordingly, when the examiner operates a focusing knob, not shown, to effect focusing, the focusing lens 144 is moved along the optical axis and the image pickup surface of the television camera 149, the image pickup surface of the CCD array sensor 158 and the focal plane of the imaging lens 153 become conjugate with the fundus Ea of the eye at a time, and with the focusing of the eye fundus image Ea', the focusing of the spot image is done.

Figure 8:
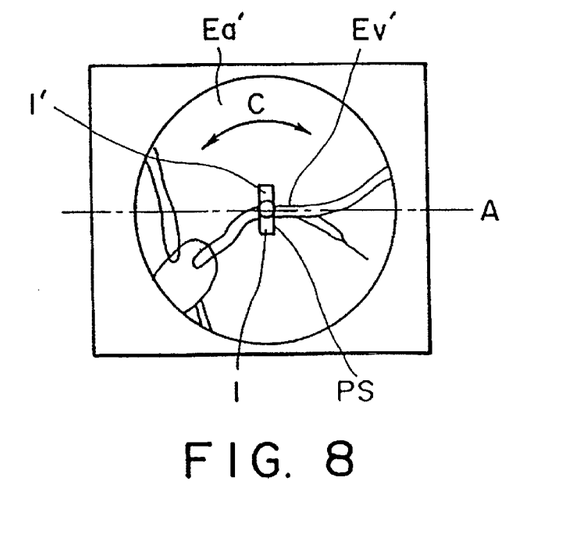
FIG. 8 is an illustration of the image of the fundus of an eye observed.

At this time, as shown in FIG. 8, the eye fundus image Ea' is displayed on the television monitor 150. The spot image PS is fixed at the center of the field of view, and for the selection of the measured region, the spot image PS is brought into coincidence with a predetermined measured region by the operating rod 142, the image rotator 131 is rotated and the blood vessel image Ev' which is the object of measurement is aligned with the axis A. The direction of the coordinates axis A indicates the direction of the line of intersection of a plane linking the centers of the optical fibers 132a, 132b, 132c in the direction of incidence with the fundus Ea of the eye, and is displayed on the television monitor 150 as an index mark for the adjustment of the image rotator 131. When the examiner rotates the image rotator 131, the image Ea' of the fundus of the eye to be examined rotates as indicated by arrow C.

Bringing the blood vessel Ev into coincidence with the axis A to thereby provide $\beta=0°$ leads to the obtainment of the following advantages (d)–(f).

(d) When from expression (2), $\beta=90°$, that is, $\cos \beta=0$, is provided, it becomes impossible to find the absolute value of the maximum blood flow speed Vmax from only the maximum frequency shifts $\Delta$fmax1 and $\Delta$fmax2 and therefore, if $\beta=0°$ is provided and the eye fundus image Ea' is rotated so as to provide $\cos \beta=1$, an unmeasurable position can be avoided.

(e) It becomes unnecessary to measure the angle $\beta$ and thus, error factors decrease and the work is simplified.

(f) As described with respect to the example of the prior art, the principle of speed detection is obtained from the interference signal between the scattered reflected light from the blood vessel wall and the scattered reflected light in the blood and therefore, even when during measurement, the fundus Ea of the eye moves in the direction of the axis A, the result of measurement will not be affected if the blood vessel Ev is made substantially parallel to the direction of the axis A.

On the other hand, when the fundus Ea of the eye moves in the axial direction orthogonal to the axis A, the signal light from the measuring laser light source 154 deviates from the blood vessel Ev in the measured region and the measured value becomes unstable, but in that case, the amount of movement of the blood vessel Ev can be detected with respect only to that direction, and in the present embodiment, tracking is effected only in that one direction by the blood vessel detecting system 159 and the image stabilizer 135.

In this case, to measure the blood flow speed accurately and quickly with respect to any blood vessel EV to be examined, it will be good if the CCD array sensor 158 for detecting the amount of movement of the blood vessel image Ev' is disposed in a direction perpendicular to the blood vessel image Ev' which is the object of measurement, and this leads to an advantage that $\beta=0°$ is provided, whereby it becomes unnecessary to use any two-dimensional sensor.

In the present embodiment, the elements of the CCD array sensor 158 are arranged in a direction orthogonal to the axis A, and when as shown in FIG. 8, the selection of a measured region has been completed, the CCD array sensor 158 of the blood vessel detecting system 159 enlarges the eye fundus image Ea' indicated by a bar-like area I in the direction orthogonal to the axis A and picks it up as the blood vessel image Ev'.

When the examiner depresses a measuring switch, not shown, to start measurement after the alignment has thus been completed, the system control unit 160 gives a tracking start command by the control means 143. At the same time, the signals of the photomultipliers 133a and 133b are introduced into the system control unit 160, and the maximum frequency shifts $|\Delta\text{fmax1}|$ and $|\Delta\text{fmax2}|$ by signal lights received from the positions 132a' and 132b' of the received beams of light on the pupil of the eye E to be examined are first found. The maximum frequency shift $|\Delta\text{fmax1}|$ is the result of the processing of the output from the photomultiplier 133a, and the maximum frequency shift $|\Delta\text{fmax2}|$ is the result of the processing of the output signal from the photomultiplier 133b.

Here, the incident signal beam of light is located at F in FIG. 7 and is provided at a location in the same direction relative to the positions of the received beams of light (the position 132b' is at an angle 0) and therefore, if usual, $\cos \beta=1$ is provided in expression (2) and the maximum blood flow speed Vmax is found from Vmax=$\{\lambda/(n\cdot\alpha)\}\cdot\|\Delta\text{fmax1}-\Delta\text{fmax2}\|$, but depending on the location of the blood vessel Ev, there is also a case where the true blood flow speed must be Vmax=$\{\lambda/(n\cdot\alpha)\}\cdot\|\Delta\text{fmax1}+\Delta\text{fmax2}\|$.

In the present embodiment, at first, as pre-measurement, the maximum blood flow speed Vmax by expression (2) is calculated in this state, whereafter the support member 161 is driven by an actuator, not shown, to thereby move the locations of the photomultipliers 133a and 133b and switch the positions of the received beams of light from the set of 132a' and 132b' to the set of 132b' and 132c'.

In the present embodiment, the signals from two adjacent ones of the three optical fibers 132a, 132b and 132c are selectively received by switching the locations of the photomultipliers 133a and 133b, and the three optical fibers 132a, 132b and 132c are disposed at equal intervals and are made symmetrical with respect to the incidence position of the probing beam. The switching method can be arbitrarily set as by providing four optical fibers and selecting and receiving the signals of two of the four optical fibers.

After the switching of the locations of the photomultipliers 133a and 133b has been effected, the system control unit 160 again introduces signals from the two photomultipliers 132a and 132b, calculates respective maximum frequency shifts |Δfmax1'| and |Δfmax2'| and calculates the maximum blood flow speed Vmax in accordance with expression (2). Assuming that the speed calculated at this time is Vmax', by selecting the set of the positions of the received beams of light as described above, it becomes possible to separate areas in which the signs of the maximum frequency shifts |Δfmax1| and |Δfmax2| switch, i.e., the area φi in FIG. 1D and the area in which the signs of |Δfmax1'| and |Δfmax2'| switch, and Vmax≅Vmax' is provided in the area wherein the signs do not switch. Also, in the area wherein the sign of one of the speeds Vmax and Vmax' switches, it becomes possible to create the relation that (the side on which the switching of the signs does not take place)>(the side on which the switching of the signs takes place).

Thus, in the apparatus of the present embodiment, the system control unit 160 can compare the two maximum blood flow speeds Vmax and Vmax' with each other to thereby determine the appropriate set of the directions of reception of the signal lights in order to find the true maximum blood flow speed. By this information, the system control unit 160 brings the locations of the photomultipliers 133a and 133b into an appropriate state (for example, when Vmax≠Vmax', the photomultipliers 133a and 133b are disposed in a state in which the greater one has been detected) and effects main measurement. In the main measurement, the measurement and calculation of the maximum blood flow speed Vmax or Vmax' are repeated at suitable time intervals, whereby continuous measurement is effected.

In the present embodiment, there has been shown a method of judging the maximum blood flow speeds Vmax and Vmax' before the main measurement, and determining the direction of light reception in the main measurement, but instead of the switching of the direction of light reception, it is also possible to cope with the situation using software for specifying the sign of expression (2), or using software for measuring the blood flow speeds Vmax and Vmax' always or alternately during the main measurement, checking the presence or absence of the reversal of the sign after the measurement or at the interval of switching, and selecting the sign of the calculation of expression (2). If the situation is coped with by the software, it will be possible to further simplify the construction of the apparatus.

Also, the present embodiment adopts an approach in which the locations of the photomultipliers 133a and 133b are moved for the switching of the direction of light reception, but alternatively, the photomultipliers may be fixedly disposed at the exit ends of the respective optical fibers and the output signals thereof may be electrically selected.

Further, the light directing system is not restricted to the optical fibers, but for example, the use of a small mirror and a lens is also possible if there is a space therefor.

Also, in the present embodiment, two adjacent directions of light reception are selected from three directions of light reception, but the selection thereof may also be effected from more directions of light reception. The entrance ends of the light receiving optical fibers may be made movable and the locations thereof may be changed to thereby obtain a similar effect. Also, it is for simplifying the subsequent calculating process that the selected directions of light reception are made symmetrical with respect to the direction of incidence of the probing beam, and this is not restrictive, but any disposition is possible. However, it is necessary in avoiding the duplication of the sign reversing area to design the directions of light reception so as not to overlap each other.

As described above, in the eye fundus blood flow meter according to the above-described embodiment, when detecting the Doppler shifts created from two directions by the blood flow on the fundus of the eye, the direction of reception of the probing beam thereof is switched and the results of the measurement of the respective blood flow speeds are compared with each other, whereby it becomes possible to avoid the problem of the sign reversal of the measuring signal. Accordingly, a correct blood flow speed can always be measured for a blood vessel at any location and in any direction in the eyeball.

What is claimed is:

1. A fundus blood flow meter comprising:

probing beam applying means for applying a probing beam to a blood vessel on a fundus of an eye to be examined;

light detecting means for detecting a scattered light of the probing beam from a vicinity of the blood vessel from two different directions of light detection;

signal processing means for obtaining information about blood flow speed in the blood vessel based on a Doppler shift signal being output from said light detecting means;

changing means for changing at least one of a direction of incidence of the probing beam onto the fundus of the eye and the two directions of light detection of said light detecting means, along a direction parallel to a direction of arrangement of the two directions of light detection; and control means for controlling the changing by said changing means, and obtaining the information about the blood flow speed by said signal processing means in each stage before and after said changing, wherein true blood flow speed is obtained based on information each obtained before and after said changing.

2. A fundus blood flow meter comprising:

probing beam applying means for applying a probing beam to a blood vessel on a fundus of an eye to be examined;

light detecting means for detecting a scattered light of the probing beam from a vicinity of the blood vessel from two different directions of light detection;

signal processing means for obtaining information about blood flow speed in the blood vessel based on a Doppler shift signal being output from said light detecting means;

changing means for changing at least one of a direction of incidence of the probing beam onto the fundus of the eye and the two directions of light detection of said light detecting means, along a direction parallel to a direction of arrangement of the two directions of light detection; and comparing means for comparing the blood flow speed information obtained by said signal processing means before and after the direction of incidence after at least one of the direction of incidence and the two directions of light detection are changed by said changing means.

3. The apparatus according to claim 2, further comprising control means for controlling said apparatus based the comparison by said comparing means.

4. The apparatus according to claim 3, wherein said control means determines at least one of the direction of incidence and the two directions of light detection based on the comparison by said comparing means and controls said apparatus to conduct a subsequent measurement of the blood flow speed.

5. The apparatus according to claim 3, wherein said probing beam applying means comprises incidence direction switching means for switching the direction of incidence of the probing beam onto the fundus of the eye.

6. The apparatus according to claim 5, wherein said control means controls said incidence direction switching means based on the comparison by said comparing means.

7. The apparatus according to claim 3, wherein said light detecting means receives the scattered light from at least two of a plurality of different locations arranged in a straight line and selects two light detecting positions from the plurality of positions.

8. The apparatus according to claim 7, wherein said control means selects two light detecting positions from the plurality of positions based on the comparison by said comparing means.

9. The apparatus according to claim 7, wherein said control control said signal processing means to selectively process the light detecting signals from two of said plurality of positions based on the comparison by said comparing means.

10. The apparatus according to claim 3, wherein said control means controls said signal processing means to perform a calculation based on the comparison by said comparing means.

11. A fundus blood flow meter comprising:

a light source which generates a probing beam;

a beam incident optical system for directing the probing beam from said light source to a blood vessel on a fundus of an eye to be examined;

light detecting elements;

a light detecting optical system for directing scattered light of the probing beam from blood cells in the blood vessel and a wall of the blood vessel from two different directions of light detecting to said light detecting elements;

a circuit unit for obtaining information about blood flow speed in the blood vessel based on a Doppler shift signal output from said light detecting elements in the two directions;

a changing mechanism for changing at least one of a direction of incidence of the probing beam onto the fundus of the eye and the two directions of light detection of said light detecting optical system, along a direction parallel to a direction of arrangement of the two directions of light detection; and a controller for controlling the changing by said changing mechanism, and obtaining the information of the blood flow speed by said circuit unit in each stage before and after said changing, wherein true blood flow speed is obtained based on the information each obtained before and after said changing.

12. The apparatus according to claim 11, wherein said changing mechanism comprises, in said light detecting optical system, a switching mirror for switching an optical path of incidence onto the fundus of the eye to be examined.

13. The apparatus according to claim 11, wherein said changing mechanism operates to switch a calculation expression used in said circuit unit.

14. A fundus blood flow meter comprising:

a light source which generates a probing beam;

a beam incident optical system for directing the probing beam from said light source to a blood vessel on a fundus of an eye to be examined;

light detecting elements;

a light detecting optical system for directing scattered light from said probing means from blood cells in the blood vessel and a wall of the blood vessel from two different directions of light detecting to said light detecting elements;

a circuit unit for obtaining information about blood flow speed in the blood vessel based on a Doppler shift signal in outputs from said light detecting elements in the two directions;

a changing mechanism for changing at least one of a direction of incidence of the probing beam onto the fundus of the eye and the two directions of light detection of said light detecting optical system, along a direction parallel to a direction of arrangement of the two directions of light detection; and wherein said changing mechanism comprises a plurality of optical fibers disposed in said light detecting optical system, and a driving mechanism for switching a disposition of said light detecting elements relative to said plurality of optical fibers.

15. A fundus blood flow meter comprising:

a light source which generates a probing beam;

a beam incident optical system for directing the probing beam from said light source to a blood vessel on a fundus of an eye to be examined;

light detecting elements;

a light detecting optical system for directing scattered light from said probing means from blood cells in the blood vessel and a wall of the blood vessel from two different directions of light detecting to said light detecting elements;

a circuit unit for obtaining information about blood flow speed in the blood vessel based on a Doppler shift signal in outputs from said light detecting elements in the two directions;

a changing mechanism for changing at least one of a direction of incidence of the probing beam onto the fundus of the eye and the two directions of light detection of said light detecting optical system, along a direction parallel to a direction of arrangement of the two directions of light detection; and a control unit for comparing the blood flow speed information obtained in said circuit unit before and after the angle of incidence of the probing beam onto the fundus of said light detecting optical system are changed by said changing mechanism.

16. A fundus blood flow meter comprising:

probing beam applying means for applying a probing beam to a blood vessel on a fundus of an eye to be examined;

light detecting means for detecting a scattered light of the probing beam from a vicinity of a blood vessel from two different directions of light detection;

signal processing means for obtaining information about blood flow speed in the blood vessel based on a Doppler shift signal being output from said light detecting means; and changing means for changing at least one of a direction of incidence of the probing beam onto the fundus of the eye and the two directions of light detection of said light detecting means;

said signal processing means measuring the blood flow speed based on outputs from said light detecting means obtained before and after said changing means performs the changing.

17. A fundus blood flow measuring method, comprising the steps of:

applying a probing beam to a blood vessel on a fundus of an eye to be examined;

detecting a scattered light of the probing beam from a vicinity of the blood vessel from two different directions of light detection;

obtaining information about blood flow velocity in the blood vessel based on a Doppler shift signal obtained in said detecting step;

changing at least one of a direction of incidence of the probing beam onto the fundus of the eye and the two different directions of light detection, along a direction parallel to a direction of arrangement of the two directions of light detection; and executing automatically said changing step, and obtaining the information about the blood flow speed in each stage before and after said changing, wherein true blood flow speed is obtained based on the information each obtained before and after said changing.

* * * * *

UNITED STATES PATENT AND TRADEMARK OFFICE
CERTIFICATE OF CORRECTION

PATENT NO. : 5,640,963                    Page 1 of 2
DATED      : June 27, 1997
INVENTOR(S): Tanaka It is certified that error appears in the above-identified patent and that said Letters Patent is hereby corrected as shown below:

COLUMN 1:

Line 28, "Red" should read --red--; and

Line 33, "$\alpha$therebetween" should read --$\alpha$ therebetween--.

COLUMN 3:

Line 1, "vector $\nu$" should read --vector $\nu 1$--; and

Line 5, "vector $\nu$" should read --vector $\nu 1$--.

COLUMN 14

Line 56, delete "after the direction of incidence"; and

Line 60, "based the" should read --based on the--.

UNITED STATES PATENT AND TRADEMARK OFFICE
CERTIFICATE OF CORRECTION

PATENT NO. : 5,640,963
DATED : June 27, 1997
INVENTOR(S) : Tanaka

It is certified that error appears in the above-identified patent and that said Letters Patent is hereby corrected as shown below:

COLUMN 15

Line 18, "control control" should read -- control means controls --.

Signed and Sealed this

Thirty-first Day of March, 1998

Attest:

BRUCE LEHMAN

Attesting Officer          Commissioner of Patents and Trademarks